(12) United States Patent
Pinel

(10) Patent No.: US 7,268,108 B2
(45) Date of Patent: Sep. 11, 2007

(54) ALPHA-MELANOCYTE STIMULATING HORMONE DERIVATIVES AND COSMETIC APPLICATION THEREOF

(75) Inventor: Anne-Marie Pinel, Toulouse (FR)

(73) Assignee: Institut European de Biologie Cellulaire, Ramonville-St-Agne (FR)

( * ) Notice: Subject to any disclaimer, the term of this patent is extended or adjusted under 35 U.S.C. 154(b) by 47 days.

(21) Appl. No.: 10/503,090

(22) PCT Filed: Jan. 31, 2003

(86) PCT No.: PCT/FR03/00300

§ 371 (c)(1),
(2), (4) Date: Apr. 22, 2005

(87) PCT Pub. No.: WO03/064458

PCT Pub. Date: Aug. 7, 2003

(65) Prior Publication Data

US 2005/0187164 A1    Aug. 25, 2005

(30) Foreign Application Priority Data

Feb. 1, 2002    (FR) ................... 02 01020

(51) Int. Cl.
*A61K 8/64* (2006.01)
(52) U.S. Cl. ......................................... 514/2
(58) Field of Classification Search .................. None
See application file for complete search history.

(56) References Cited

U.S. PATENT DOCUMENTS

| | | | |
|---|---|---|---|
| 5,674,839 A | 10/1997 | Hruby et al. | |
| 5,683,981 A | 11/1997 | Hadley et al. | |
| 5,714,576 A | 2/1998 | Hruby et al. | |
| 5,830,994 A | 11/1998 | D'Hinterland et al. | |
| 6,054,556 A | 4/2000 | Huby et al. | |
| 6,245,342 B1 * | 6/2001 | Golz-Berner et al. | 424/401 |
| 6,337,315 B1 * | 1/2002 | Mahe et al. | 514/2 |

FOREIGN PATENT DOCUMENTS

| | | |
|---|---|---|
| FR | 2 753 707 A | 3/1998 |
| WO | WO98/12212 | 3/1998 |
| WO | WO-99/54358 A | 10/1999 |
| WO | WO-01/90140 A | 11/2001 |
| WO | WO2002064734 * | 8/2002 |
| WO | WO 03/006620 * | 1/2003 |

OTHER PUBLICATIONS

Haskell-Luevano et al., J. Med. Chem., 40, pp. 2133-2139 (1997).
M.E. Hiltz et al., Peptides, 11, pp. 979-982 (1990).
H. Rink, Tetrahedron Letters, 28(33), pp. 3787-3790 (1987).
G.R. Matsueda et al., Peptides 2, pp. 45-50 (1981).
J.A. Beavo et al., Molecular Pharmacology, 6, pp. 597-603 (1970).
W. Montague et al., Biochem J., 122, pp. 115-120 (1971).
"Melanocyte-Stimulating Hormone (MSH)", extracted from www.ultranet.com/~jkimball/BiologyPages/M/MSH.html (Aug. 27, 2001).
Sahm et al., J. Pharm Pharmacol, 48(2), pp. 197-200 (Feb. 1996) (abstract).
R.A. Sturm et al., Gene, 277(1-2), pp. 49-62 (Oct. 17, 2001) (abstract).
Z. Abdel-Malek et al., Pigment Cell Res 2000, 13 Suppl 8, pp. 156-162 (abstract).
T.A. Luger et al., Ann NY Acad Sci 2000, 917, pp. 232-238 (abstract).

* cited by examiner

*Primary Examiner*—Cecilia J. Tsang
*Assistant Examiner*—Christina Marchetti Bradley
(74) *Attorney, Agent, or Firm*—Birch, Stewart, Kolasch & Birch, LLP

(57) ABSTRACT

The invention relates to peptides of formula (I) $R-V^1-Ala^2-His^3-X^4-Y^5-Trp^5-NH2$ wherein R represents a hydrogen atom or a protective group which can be chosen from among a benzoyl group, a tosyl group, a benzene sulfonyl group, a benzyloxycarbonyl group or a pyridinepropionyl group; V represents a natural amino acid or not chosen from among norleucine, norvaline and 2-N-Me-norleucine, X represents a natural amino acid or not having an aromatic character chosen from among phenylalanine, 1-naphtylalanine, 2-naphtylalanine, phenylglycine, benzothienylalanine, 4,4'-biphenylalanine, 3,3-diphenylalanine, homophenylalanine, indanylglycine, 4-methylphenylalanine, thienylalanine, p-nitrophenylalanine, halogenophenylalanine of configuration L or D; Y represents a natural amino acid of configuration L, having a basic character chosen from among arginine, lysine or ornithine, the enantiometers or diastercoisomers, and the mixtures thereof, including racemic mixtures. The invention also relates to a method for the preparation and application thereof in the field of therapeutics or cosmetics.

6 Claims, 4 Drawing Sheets

Effect of peptide no. 1 on IL-8 released by SAEC

ALPHA-MELANOCYTE STIMULATING HORMONE DERIVATIVES AND COSMETIC APPLICATION THEREOF

The present invention relates to pseudopeptides derivatives which reproduce the peripheral effects of alpha-MSH (Melanocyte Stimulating Hormone), to the preparation thereof and to the therapeutic and cosmetic application thereof.

Alpha-MSH is a substance that is naturally produced by the human body and is known to have a very large number of physiological activities: antipyretic, anti-inflammatory and pigmenting activities.

As a mediator, alpha-MSH has specific receptors, five of which have been described and each possess 7 transmembrane domains. In the skin, the abovementioned activities involve the "melanocortin-1" receptor (MC-1r). At this level, the binding of alpha-MSH induces the activation of a G protein (exhibiting an alpha-subunit of Gγs type) which will itself stimulate adenylyl cyclase and thus produce cyclic adenosine monophosphate (or cAMP).

The production of cAMP induces the activation of type A protein kinases, which will activate, by phosphorylation, the proteins capable of binding to cAMP response elements (or CREB) of the DNA of the cell's genes. This results in the expression of mediators which then exert their effects on the target cells.

In mammals, the coloration of the skin and of the hair is due to a common category of pigments: melanins. These melanins are produced in the skin by melanocytes, cells which are located at the level of the basement membrane of the epidermis and in the hair follicles. Melanin synthesis is controlled by the activity of an enzyme: tyrosinase. It is the production of this enzyme (and also that of the associated enzymes: TRP-1 & TRP-2) that is stimulated by the binding of alpha-MSH to its receptor MC-1.

The production of melanin by tyrosinase takes place in cytoplasmic organelles: premelanosomes. Once they are filled with melanins, these organelles are called melanosomes and are transferred, via the dendrites of the melanoctye, to the neighboring cells: the keratinocytes. The melanin is thus distributed within the epidermis, providing tanning and protection thereof.

Melanin, a natural pigment recognized for its free-radical-scavenging properties and solar radiation-absorbing properties, is the physiological protective agent of the skin. No available compound exists in dermocosmetology which can stimulate the production of this pigment in humans.

In addition, the mechanism of the anti-inflammatory effects of alpha-MSH have not been completely elucidated, but many experimental facts converge and result in the idea that alpha-MSH, by binding to the MC-1 receptor, inhibits the induction of NOSi (or $NOS_2$) and of NFKB and induces the expression of the mRNA followed by the production of the anti-inflammatory cytokine IL-10. This cytokine opposes the release of inflammatory cytokines such as IL-1, IL-6, IL-8, TNF-α or γINF.

Keratinocytes, which constitute 95% of the cell population of the epidermis, are considered to be IL-1 reservoirs and have MC-1 receptors at their cell surface. Thus, the binding of alpha-MSH to these receptors allows modulation of local inflammatory phenomena.

Alpha-MSH is a tridecapeptide of formula Acetyl-$Ser^1$-$Tyr^2$-$Ser^3$-$Met^4$-$Glu^5$-$His^6$-$Phe^7$-$Arg^8$-$Trp^9$-$Gly^{10}$-$Lys^{11}$-$Pro^{12}$-$Val^{13}$-$NH_2$ (SEQ ID NO: 3) (where Ser=serine, Tyr=tyrosine, Met=methionine, Glu=glutamic acid, His=histidine, Phe=phenylanifle, Arg=arginine, Trp=tryptophan, Gly=glycine, Lys=lysine, Pro=proline and Val=valine). A very large number of scientific studies have established the active sequences of alpha-MSH, which are conventionally described as being the heptapeptide 4-10 for melanotropic effects (Haskell-Luevano et al. *J. Med. Chem.* 1997, 40, 2133-2139) and the tripeptide 11-13 for the antiinflammatory effects (Hiltz M. E. and Lipton J. M. *Peptides* 1990, 11, 979-982).

In addition, the recent studies have led various authors to file patents disclosing cyclized structures (Hruby et al. U.S. Pat. No. 5,674,839 and U.S. Pat. No. 6,054,556).

The aim of the present invention is thus to provide small linear pseudopeptide compounds exhibiting melanotropic and/or anti-inflammatory, anti-allergic activities.

More precisely, a subject of the invention is novel peptides corresponding to formula (I)

$$R\text{-}V^1\text{-}Ala^2\text{-}His^3\text{-}X^4\text{-}Y^5\text{-}Trp^6\text{-}NH_2 \quad (I)$$

in which

R represents a hydrogen atom or a protective group which can be chosen from an acetyl group, a benzoyl group, a tosyl group, a benzenesulfonyl group, a benzyloxycarbonyl group or a pyridinepropionyl group;

V represents a natural or unnatural, L-configuration, amino acid chosen from norleucine, norvaline and 2-N-Me-norleucine;

X represents a natural or unnatural, L- or D-configuration, amino acid which is aromatic in nature, chosen from phenylalanine, 1-naphthylalanine, 2-naphthylalanine, phenylglycine, benzothienylalanine, 4,4'-biphenylalanine, 3,3-diphenylalanine, homophenyl-alanine, indanylglycine, 4-methylphenylalanine, thienylalanine, p-nitrophenylalanine, and halophenyl-alanine where the halogen may be a chlorine, bromine, iodine or fluorine atom in the position meta, ortho or para to the phenyl group;

Y represents a natural, L-configuration amino acid which is basic in nature, chosen from arginine, lysine or ornithine.

The amino acids Ala, His and Trp at positions 2, 3 and 6, respectively, in the peptide of formula (I) are in the L configuration.

The peptides of formula (I) may comprise one or more asymmetric carbon atoms. They may exist in the form of enantiomers or of diastereoisomers. These enantiomers and diastereoisomers and the mixtures thereof, including racemic mixtures, are part of the invention.

These novel peptides possess activity with respect to the stimulation of pigmentation and/or with respect to the limitation of local inflammatory phenomena, in the skin or the mucous membranes.

In particular, the peptides according to the invention are useful in the prevention and/or the treatment of pathologies such as atopic dermatitis, psoriasis, vitiligo, erythema, inflammatory alopecia, eczema or asthma, which are initiated at the cellular level and can be attenuated by means of the direct intervention of compounds which mimic the natural mediators.

The peptides which are the subject of the present invention therefore constitute an extraordinary innovation in terms of skin care.

The present invention thus also relates to the use of one or more peptides of formula (I), for producing a medicinal product having an anti-inflammatory and/or anti-allergic effect, and also the use of one or more peptides of formula (I), for producing a cosmetic product having melanotropic activity.

Among the compounds of formula (I) which are subjects of the present invention, mention may be made of the preferred compounds which are defined as follows:

R represents a protective group which can be chosen from an acetyl group, a benzenesulfonyl group, a tosyl group or a pyridinepropionyl group, V represents a natural or unnatural amino acid chosen from norleucine and 2-N-Me-norleucine, which is in the L configuration, X represents a natural or unnatural amino acid which is aromatic in nature, chosen from phenylalanine, 2-naphthylalanine, homophenylalanine, thienylalanine or p-nitrophenylalanine, and which is in the D or L configuration, Y represents a natural L-configuration amino acid which is basic in nature, chosen from arginine or lysine.

The alanine, histidine and tryptophan at positions 2, 3 and 6, respectively, in the peptide of formula (I) are in L configuration.

In accordance with the invention, the compounds of general formula (I) can be prepared according to various methods known to those skilled in the art, in particular by methods of chemical synthesis in solution or on a solid support. Synthesis on a support with resin is particularly suitable. Among the resins which may be used, mention may be made of resin of Rink amide type (or 4-(2'-4'-dimethoxyphenyl-fmoc-aminomethyl)phenoxy resin) (H. Rink, *Tetrahedron Let.*, 1987, 28, 3787) and MBHA resin (or 4-methylbenzhydrylamine resin) (G. R. Matsueda et al. *Peptides*, 1981, 2, 45).

The starting products are protected amino acids. The protective groups can be an acetyl (Ac) group or a 9-fluorenylmethoxycarbonyl (Fmoc) group on the main amine function, or a tert-butyloxycarbonyl (Boc) group, a trityl (Trt) group or a 2,2,5,7,8-pentamethylchroman-6-sulfonyl (Pmc) group on the functions of the side chains. The washing, coupling and deprotection techniques are well known to those skilled in the art. They are, for example, described in Fmoc Solid Phase Peptide Synthesis: A Practical Approach: W. C. Chan and P. D. White (Oxford University Press) or Chemical Approaches to the Synthesis of Peptides and Proteins—Paul Lloyd-Williams, Fernando Albericio, Ernest Giralt (CRC Press Boca Raton, N.Y.).

Figure 1:
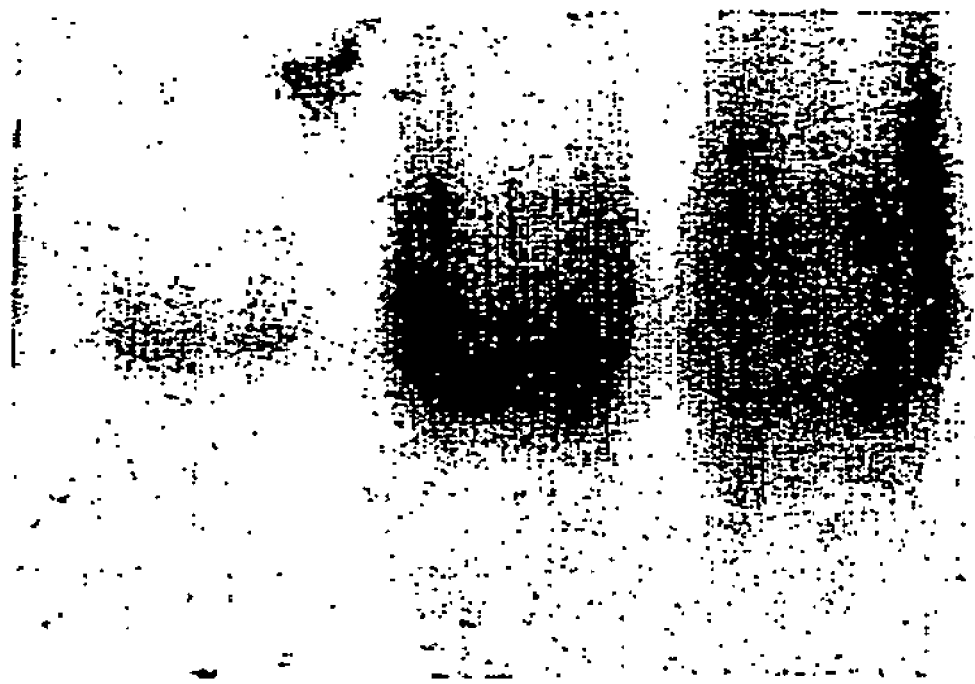
FIG. 1: The action of peptide no. 1 and of alpha-MSH on the production of tyrosinase was demonstrated in vitro on maintained human melanocytes. The production of tyrosinase was followed on the M4Be line by western blotting using an anti-human tyrosinase antibody. The presense of tyrosinase is visualized by chemiluminescence using an ECL detection kit (Amersham Pharmacia Biotech, ref RPN2109), which exposes a photographic film.

The following examples illustrate the present invention.

EXAMPLE 1

Compound No. 1 in the Table (R=Ac, V=Nle, X=DPhe, Y=Arg, Ala$^2$, His$^3$ and Trp$^6$ in the L Configuration)

This peptide is synthesized by solid-support synthesis with a Rink amide-type resin, the functionalization of which is between 0.3 and 0.6 mmol/g of resin.

Firstly, the Rink amide resin is prepared by washing with DMF (2 washes) and then the deprotection is performed as described below. For each amino acid to be coupled, the steps consisting in coupling of the amino acid, washing of the resin, deprotection of the amine function of the main chain of the amino acid, and again washing of the resin are repeated.

Coupling: 2 equivalents of BOP (or HBTU), 2 equivalents of DIEA (or NMM) and 2 equivalents of Fmoc-AA-OH for 2 hours in DMF.

Washing: 2 washes with DMF, 1 wash with methanol, 2 washes with dichloromethane and 1 wash with DMF.

Deprotection: 80/20 DMF/piperidine mixture with 2% of ethanediol (free-radical scavenger), once for 3 minutes, and then 7 minutes.

Washing: (idem above).

After the various amino acid couplings, the peptide is cleaved from the resin using a 50/50 TFA/dichloromethane mixture with 2% of ethanediol, for 1 h 30 min.

The dichloromethane and the TFA are evaporated off under a stream of nitrogen, and then precipitation with diethyl ether and purification of preparative liquid chromatography, with a C18 reverse-phase column, are performed.

The synthesis of Ac-Nle-Ala-His-DPhe-Arg-Trp-NH$_2$ is carried out with the following protected amino acids (Fmoc-AA-OH):

Fmoc-Trp(Boc)-OH
Fmoc-Arg(Pmc)-OH
Fmoc-DPhe-OH
Fmoc-His(Trt)-OH
Fmoc-Ala-OH
Ac-Nle-OH Abbreviations:
Fmoc: 9-fluorenylmethoxycarbonyl
TFA: trifluoroacetic acid
DMF: dimethylformamide
BOP: 1-benzotriazolyloxytris(dimethylamino)-phosphonium hexafluorophosphate
HBTU: 2-(1H-benzotriazole-1-yl)-1,1,3,3-tetra-methyluronium hexafluorophosphate
DIEA: diisopropylethylamine
NMM: N-methylmorpholine The desired peptide is obtained, the analytical results for which are given in the table which follows.

EXAMPLE 2

Compound No. 2 in the Table (R=Ac, V=Nle, X=DPhe, Y=Lys, Ala$^2$, His$^3$ and Trp$^6$ in the L Configuration)

This peptide is synthesized by solid-support synthesis with a Rink amide-type resin, the functionalization of which is between 0.3 and 0.6 mmol/g of resin.

The synthesis is carried out according to the same procedure to that described in Example 1. The amino acids used for the synthesis are as follows:

Fmoc-Trp(Boc)-OH
Fmoc-Lys(Boc)-OH
Fmoc-DPhe-OH
Fmoc-His(Trt)-OH
Fmoc-Ala-OH
Ac-Nle-OH The analytical characteristics of this peptide are given in the table which follows.

The table which follows illustrates the chemical structures and reiterates the analytical results of some compounds of the invention and also their molecular masses (MM) expressed in g/mol.

An analysis by high performance liquid chromatography (HPLC) and an analysis by mass spectrometry (MS) were performed for each of the compounds of the invention.

HPLC:

Stationary phase: C18 reverse-phase-type column, the dimensions of which are: 4.6×50 mm, 3.5 μm.
Mobile phase: Binary mixture made of water (with 0.1% of TFA) and of acetonitrile (with 0.1% of TFA).
Method: Gradient over 12 minutes, of 0% to 80% of acetonitrile (0.1% of TFA).
Detection wavelength: 214 nm.

In the table, the purities are expressed as relative percentage with respect to the surface area of the peaks of the crude product before purification, and the retention times (R.T.) are expressed in minutes.

M.S:

Positive electrospray, with a cone voltage of 9V, a source temperature at 120° C. and a scanning time of 6 seconds.

The table reports the value of the molecular ion $[M+H]^+$ and, in some cases, the doubly-charged ion $[M+2H]^{2+}$.

$Ala^2$: Fmoc-Ala-OH
$Ala^1$: Ac-Nle-OH, Fmoc-Nle-OH in the case of an end protection other than acetyl protection.

In this case, the end protections (R) will be introduced, after a deprotection step, by coupling, using the following reagents: benzenesulfonyl chloride, pyridinepropionyl chloride and tosyl chloride.

The peptides of the invention were the subject of pharmacological trials for determining their effects, after their innocuity had been confirmed by suitable toxicity tests and tolerance tests.

1. The affinity of the peptides in the table for the MCl-r receptor was demonstrated, in vitro, on a melanocyte line, by means of the production of cAMP.

Determination of the effect of the peptides according to the invention, in comparison with alpha-MSH, on the activation of adenylyl cyclase by melanocytes maintained in vitro was carried out using a methodology in particular described in Beavo J. A. et al. *Mol. Pharmacol.*, 6(6), 597-603, 1970 and in Montague W. Cook J. R., *Biochem J.*, 122(1), 1971. Murine melanocytes (line S91 Cloudman) capable of synthesizing melanins are used.

The cAMP production was followed by the EIA method (Amersham Pharmacia Biotech, Biotrack kit ref RPN225) according to the supplier's recommendations. We determined the percentage response induced by the various molecules that had been screened, compared to alpha-MSH (100%). All the experimental conditions were carried out in duplicate.

TABLE $R-V^1-Ala^2-His^3-X^4-Y^5-Trp^6-NH_2$ (I)

| | | | | | HPLC | | MS | | MM |
|---|---|---|---|---|---|---|---|---|---|
| No | R | V | X | Y | Purity | R.T. | $[M+H]^+$ | $[M+2H]^{2+}$ | g/mol |
| 1 | Ac | Nle | Dphe | Arg | 81% | 6.80 | 870.7 | 435.99 | 899 |
| 2 | Ac | Nle | DPhe | Lys | 88% | 6.63 | 842.75 | 422.13 | 841 |
| 3 | Ac | Nle | Dthi | Arg | 86% | 5.73 | 876.68 | 438.89 | 875 |
| 4 | BzlSO$_2$ | Nle | DPhe | Arg | 96% | 6.46 | 968.66 | 485.21 | 967 |
| 5 | Tos | Nle | DPhe | Arg | 91% | 6.51 | 969.70 | 486.23 | 968 |
| 6 | BzlSO$_2$ | Nle | DPhe | Lys | 84% | 6.32 | 940.77 | 471.05 | 939 |
| 7 | BzlSO$_2$ | Nle | DpNO$_2$Phe | Lys | 74% | 6.60 | 985.50 | 493.6 | 984 |
| 8 | BzlSO$_2$ | Nle | DThi | Lys | 94% | 15.74 | 919.63 | 460.62 | 918 |
| 9 | Ac | Nle | DThi | Lys | 86% | 5.57 | 821.86 | 411.52 | 820 |
| 10 | PyrProp | Nle | DpNO$_2$Phe | Lys | 84% | 5.45 | 978.7 | 490.2 | 977 |
| 11 | PyrProp | Nle | DpNO$_2$Phe | Arg | 86% | 5.57 | 1006.5 | 504.3 | 1005 |
| 12 | Ac | Nle | L2, Nap | Lys | 74% | 7.84 | 865.69 | 433.63 | 864 |
| 13 | Ac | MeNle | DHomoPhe | Arg | 75% | 7.20 | 899.71 | 450.95 | 898 |
| 14 | Ac | Nle | DHomoPhe | Arg | 88% | 6.95 | 885.65 | 443.52 | 884 |

In this table:
Ac represents an acetyl group,
BzlSO$_2$ represents a benzenesulfonyl group,
PyrProp represents a pyridinepropionyl group,
Tos represents a tosyl group,
DHomoPhe represents homophenylalanine in the D configuration,
DThi represents thienylalanine in the D configuration,
DpNO$_2$Phe represents p-nitrophenylalanine in the D configuration,
L2, Nap represents 2-naphthylalanine in the L configuration,
DPhe represents phenylalanine in the D configuration,
Nle represents norleucine in the L configuration,
NMe-Nle represents 2-N-Me-norleucine in the L configuration.

For these compounds, it is possible to carry out a synthesis on a support with a Rink amide-type resin, as described in Example 1.

The amino acids are introduced in protected form onto the side chains if necessary, the main amine function being protected with an Fmoc group. The molecules used for these syntheses are, according to the position:
$Trp^6$: Fmoc-Trp(Boc)-OH
$Y^5$: Fmoc-Arg(Pmc)-OH, Fmoc-Lys(Boc)-OH
$X^4$ Fmoc-DPhe-OH, Fmoc-D-pNO$_2$Phe-OH, Fmoc-DThi-OH, Fmoc-L2, Nap-OH, Fmoc-DHomoPhe-OH
$His^3$: Fmoc-His(Trt)-OH

| No. of the compound according to Example 3 | cAMP production (as % of α-MSH) |
|---|---|
| α-MSH | 100 |
| 1 | 80 |

-continued

| No. of the compound according to Example 3 | cAMP production (as % of α-MSH) |
|---|---|
| 2 | 40 |
| 3 | 10 |
| 4 | 70 |
| 5 | 100 |
| 6 | 55 |
| 7 | 100 |
| 8 | 65 |
| 9 | 75 |
| 10 | 115 |
| 11 | 150 |
| 12 | 50 |
| 13 | 55 |
| 14 | 45 |

The action of peptide no. 1 and of alpha-MSH on the production of tyrosinase was demonstrated in vitro on maintained human melanocytes. The production of tyrosinase was followed on the M4Be line by western blotting using an anti-human tyrosinase antibody.

After culturing for 24 hours, alpha-MSH or peptide no. 1 is added to the cells, at a final concentration of $10^{-7}$ M. 24 hours later, these cells are detached by scraping and lysed in 50 mM $NaH_2PO_4$ buffer, pH 6.8+1% Triton X100+1 mM PMSF. The amount of proteins in the various samples is determined by assaying with bicinchoninic acid. 100 μg of sample are loaded per well of a 15% acrylamide/bisacrylamide electrophoresis gel. The samples are migrated for 3 hours at 70 mA. Transfer onto a nitrocellulose membrane (Schleicher & Schuell, ref Protan) is carried out overnight at 10 V. The membrane is blocked with buffer at pH 7.6 (22 mM Tris; 1.37 M NaCl; 1M HCl)+0.1% Tween+5% of BSA, for an hour at 37° C. The revelation is carried out, firstly, with an anti-human tyrosinase goat antibody (Santa Cruz, ref SC-7833) diluted to 1/1000 at 4° C. overnight. Incubation is then carried out with a peroxidase-coupled anti-goat immunoglobulin antibody (Sigma, ref A8919) diluted to 1/10000 at ambient temperature for 1 hour. The presence of tyrosinase is visualized by chemiluminescence using an ECL detection kit (Amersham Pharmacia Biotech, ref RPN2109), which exposes a photographic film (Amersham Pharmacia Biotech, ref RPN2103K) shown in FIG. 1/1.

2. A double-blind study of the melanostimulant effects by topical administration of peptide no. 1 in the table was carried out in humans.

A gel of peptide no. 1 at 10 ppm and its placebo were applied, twice a day for 3 weeks, to the inner face of the forearms of twelve normal volunteers who had given their informed consent. Since the arms were not exposed to the sun, they were given an exactly calibrated artificial solar exposure of 0.6 MED (minimum erythema dose) once a day from the 16th to 20th day.

24 h after the final treatment, a clinical evaluation of the treated regions was carried out blind, and the intensity of coloration was marked according to a five-level index scale. A biopsy sample was then taken in order to quantify the melanin produced and to evaluate the ultrastructural consequences of the treatment.

The quantification of the epidermal melanin was carried out on histological sections by image analysis after labeling with $AgNO_3$. Only the active layers of the epidermis were analyzed (from the stratum germinativum to the stratum spinosum), using the Leica Quantimet after digitization (Sony CCD camera).

The ultrastructural analysis of the melanocytes and melanosomes was carried out by electron microscopy. A double-contrast technique was used on the thin sections, which were then observed at magnifications ranging up to ×12000 (Jeol 1200EX).

Compared to the placebo, peptide no. 1 in the table induces a statistically significant increase in the browning of the skin (tanning) of 54% ($p<0.05$, Student's t test). Clinical observation of the treated regions revealed no sign of intolerance.

Compared to the placebo, peptide no. 1 in the table induces a statistically significant increase (+68%, $p<0.01$) in the amount of melanin in the epidermis of the volunteers. Analysis of variance according to the Fisher test reveals a very significant produced effect with a risk of less than 1%.

Comparison of the individual results reveals, moreover, an excellent correlation between the two methods.

The ultrastructrual analysis of the melanocytes reveals a considerable influence of the treatment, with large cells, a developed nucleus exhibiting little heterochromatin, very abundant cellular organelles and dendrites loaded with eumelanosomes. All these signs reflect an intense activity of melanin biosynthesis, which is completely physiological.

The study of the melanosomes in the keratinocytes shows that they naturally accumulate at the apical level of the cell nucleus, constituting a typical "nuclear parasol".

Peptide no. 1 in the table, applied topically, is found to be capable of significantly stimulating cutaneous melanogenesis in humans. It is, moreover, completely tolerated at the local level.

3. The anti-inflammatory activity was demonstrated as follows:

On the skin, irritants such as surfactants are responsible for inflammatory reactions characterized by the extra cellular expression of cytokines such as interleukin-1-alpha (IL-1α). The SDS-stimulated keratinocytes culture model was used to assess the anti-inflammatory potential of peptide no. 1 in the table.

NCTC 2544 human keratinocytes are placed in culture with peptide no. 1 in the table, at a concentration of $10^{-6}$ M, for 72 h. After rinsing, the SDS is introduced at a concentration of 85 mg/l and left in contact for 24 h.

The extracellular IL-1α levels in the supernatant are determined by the ELISA method (Immunotech, ref 0755), chosen for the lack of interference with SDS.

Effect of peptide no. 1 in the table on the release of IL-1α by SDS-stimulated NCTC2544 keratinocytes:

|  | Controls | Treated peptide no. 1 at $10^{-6}$ M |
|---|---|---|
| Pg of IL-1α/$10^9$ cells | 38 | 22 |

Peptide no. 1 reduces by approximately 42% the expression of IL-1α by SDS-stressed keratinocytes in culture.

4. The effect of peptide no. 1 in the table on photo-induced erythema in vivo in humans is determined.

14 normal adult volunteers of both sexes, of phototype classes III & IV (light and intermediate) and of Individual Typological Angle (ITA°) of 50 to 28° gave their informed consent to participate in the study.

The treatment consists of a topical application to the inner face of the forearm twice/day for 2 weeks at a rate of 2 μl/cm$^2$ over 75 cm$^2$. During the study, the arm is protected against any exposure to the sun.

The solar radiation is provided by a 150 W xenon arc lamp with a UVA & B spectrum ranging from 290 to 390 mm. Six doses of light intensity with a geometrical progression of 25% are applied to the treated regions through liquid light guides.

The colorimetrical measurements are made using the Chromameter™ CR 300. The chromaticity coordinates (L; a & b*) are determined with respect to a non-irradiated nearby region. A differential $\Delta a^* > 2.5$ makes it possible to define with precision the MED.

24 hours after the final treatment, the treated and control regions are irradiated with increasing doses of UV calculated to straddle the MED of each individual. After 24 h and 72 h, the irradiated region is evaluated by means of calorimetric measurements.

The evaluation criterion is the MED: the lowest dose of UV A & B which causes erythema.

A statistically significant increase in the MED is observed with the treatment with peptide no. 1 in the table.

Evaluation of the MED after exposure to UV A & B in $J/cm^2$:

|  | Control region | Treated region |
|---|---|---|
| 24 h after exposure | 1.5 | 1.8* |
| 72 h after exposure | 1.5 | 1.7 |

*statistically significant values (LSD and paired "t" test, $p < 0.05$)

The application of peptide no. 1 in the table, in the gel, topically, makes it possible to increase the skin's resistance to the appearance of erythema caused by an excessive solar irradiation.

It therefore appears that the peptides of the invention have an anti-inflammatory, anti-allergic and melanotropic activity.

The peptides of the invention can therefore be used for preparing medicinal products intended to treat allergies, in particular skin allergies, inflammatory reactions and melanogenesis conditions. These medicinal products thus find their use in therapeutics, in particular in the prevention and/or the treatment of atopic dermatitis, psoriasis, vitiligo, erythema, and in particular photo-induced erythema, inflammatory alopecia, eczema and asthma.

According to another of its aspects, the present invention relates to pharmaceutical compositions containing, as active principle, a peptide according to the invention. These pharmaceutical compositions may in particular be suitable for local application to the skin and the mucous membranes.

Thus, these pharmaceutical compositions contain an effective dose of a peptide according to the invention, and one or more suitable pharmaceutical excipients.

Said excipients are chosen according to the pharmaceutical form and the mode of administration desired.

In the pharmaceutical compositions of the present invention for oral, sublingual, subcutaneous, intramuscular, intravenous, topical, intratracheal, intranasal, transdermal (patch) or rectal administration, the active principle of formula (I) above, or any salt or hydrate thereof, can be administered in unit administration form, as a mixture of conventional pharmaceutical excipients, to animals and to human beings for the prophylaxis or the treatment of the above conditions or diseases. The suitable unit administration forms comprise forms for oral administration, such as tablets, gel capsules, powders, granules and oral solutions or suspensions, sublingual, buccal, intratracheal and intranasal administration forms, subcutaneous, intramuscular or intravenous administration forms, and rectal administration forms. For topical application, the compounds according to the invention can be used in creams, ointments, liquid aerosols or sprayed aerosols (sprays), gels, lotions and patches.

Whatever the route of administration, the dose of active principle administered per day can reach 0.5 mg/kg, given in one or more doses.

There may be particular cases where higher or lower dosages are suitable, and such dosages also belong to the invention. According to usual practice, the dosage suitable for each patient is determined by the physician according to the method of administration and the weight and the response of said patient.

Where a solid composition is prepared in the form of tablets, the main active ingredient is mixed with a pharmaceutical excipient, such as gelatin, starch, lactose, magnesium stearate, talc, gum arabic, or the like. The tablets can be coated with sucrose, with a cellulose derivative or with other materials. The tablets can be produced by various techniques, direct compression, dry granulation, wet granulation or hot melting.

A preparation of gel capsules is obtained by mixing the active ingredient with a diluent and pouring the mixture obtained into soft or hard gel capsules.

For parenteral administration, use may be made of aqueous suspensions, isotonic saline solutions or sterile and injectable solutions which contain pharmacologically compatible dispersing agents and/or wetting agents, for example propylene glycol or butylene glycol.

According to another of its aspects, the present invention also relates to a method for treating the pathologies indicated above, which comprises the administration of a peptide according to the invention or a pharmaceutically acceptable salt thereof.

A cosmetic composition comprising a compound of formula (I) which can be administered mucosally or topically is also part of the invention, as is the use of a compound of formula (I), for preparing a cosmetic product having a melanotropic effect.

According to a final aspect, a subject of the invention is dermocosmetic compositions comprising a peptide of formula (I) according to the invention, for topical application, which can be in the form of solutions, lotions, emulsions, liquid aerosols or sprayed aerosols (sprays), gels or creams, which can be used in particular as an agent for preparing the skin against exposure to the sun, a tanning accelerator, an agent for recoloring white hair, an agent for soothing the skin, an anti-erythema agent.

It should be understood that the pharmaceutical compositions, cosmetic products or dermocosmetic compositions which are subjects of the invention as described above, containing mixtures of peptides according to the invention, are also part of the invention.

5. Effect of the stimulation of SAEC[1] cells from normal individuals, or of polynuclear neutrophils and monocytes from cortico-dependant patients suffering from severe asthma, by peptide no. 1 compared with dexamethasone:

[1] SAEC: Small Airway Epithelial Cells a) Epithelial Cells:

SAEC (primary human epithelial cells in culture) origin: small bronchi of normal individuals, Expansion in flasks, trypsinization and transfer to wells (48-well plate), At confluency, incubation in wells for 24 h, Non-stimulated, +TNFalpha (25 ng/ml)+peptide no. 1 in the table from $10^{-5}$ M to $10^{-8}$ M+dexamethasone $10^{-7}$ M, Recovery of the supernatants, storage at −20° C., Assaying of IL-8 using an ELISA kit.

Figure 2:
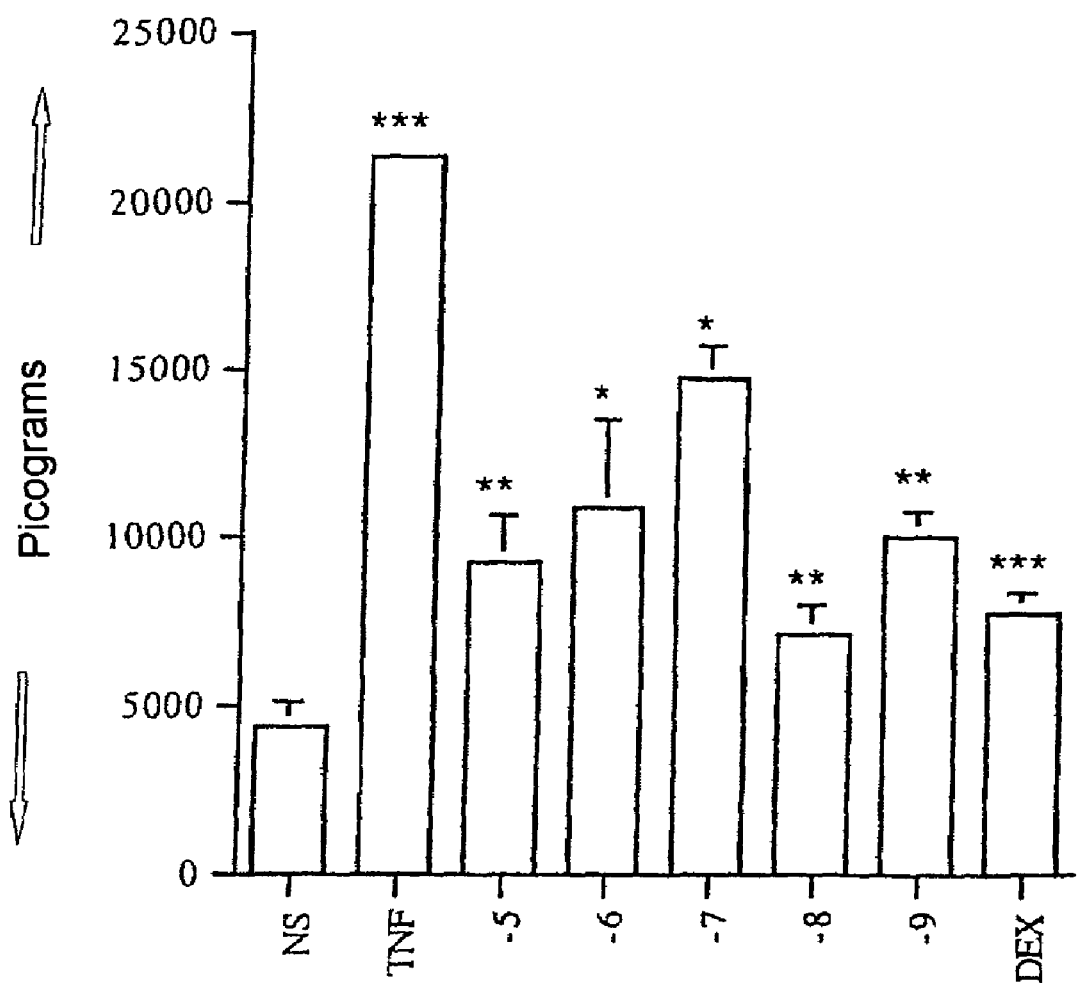
FIG. 2: The effect of the stimulation of SAEC cells by peptide no. 1 is respresented (NS=non-stimulated, DEX=dexamethasone).

The effect of the stimulation of SAEC cells by peptide no. 1 is represented in FIG. 2 (NS=non-stimulated, DEX=dexamethasone).

b) 8 Cortico-Dependant Patients Suffering from Severe Asthma:

Heparized blood: 30 ml,
Separation on Percoll gradient (62-72%),
Monocytes and neutrophiles >95% viability >99%,
Cells taken up and washed in RPMI,
107 cells/ml, incubation in wells for 24 h,
Non-stimulated, +peptide no. 1 in the table from $10^{-6}$ M to $10^{-8}$ M+dexamethasone $10^{-7}$ M,
Recovery of the supernatants, storage at −20° C.,
Assaying of IL-8 using an ELISA kit.

Figure 3:
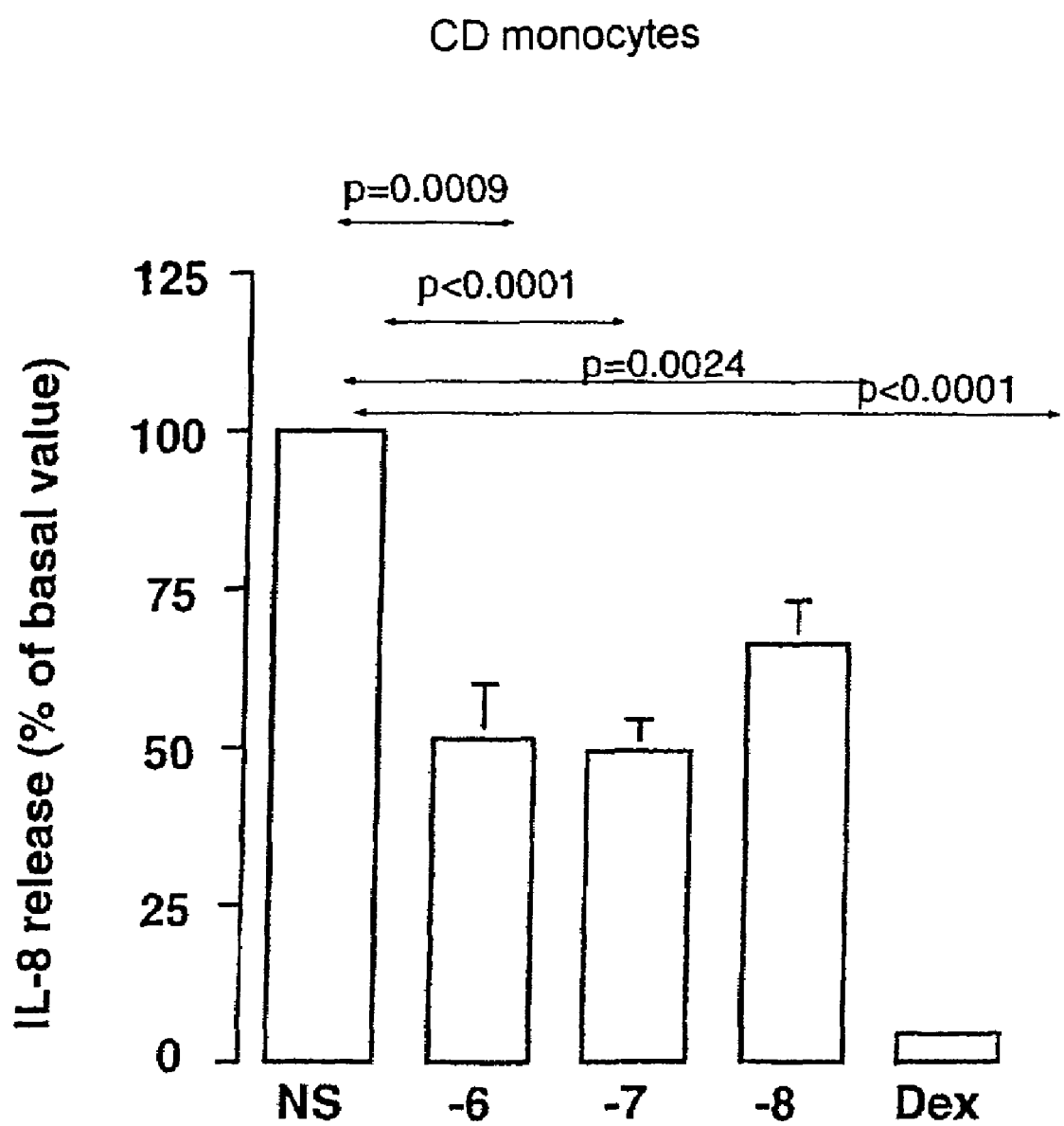
FIG. 3: The effect of the stimulation of cortico-dependant (CD) monocytes by peptide no. 1 is represented (NS=non-stimulated, DEX=dexamethasone).

The effect of the stimulation of cortico-dependant (CD) monocytes by peptide no. 1 is represented in FIG. 3 (NS=non-stimulated, DEX=dexamethasone).

Figure 4:
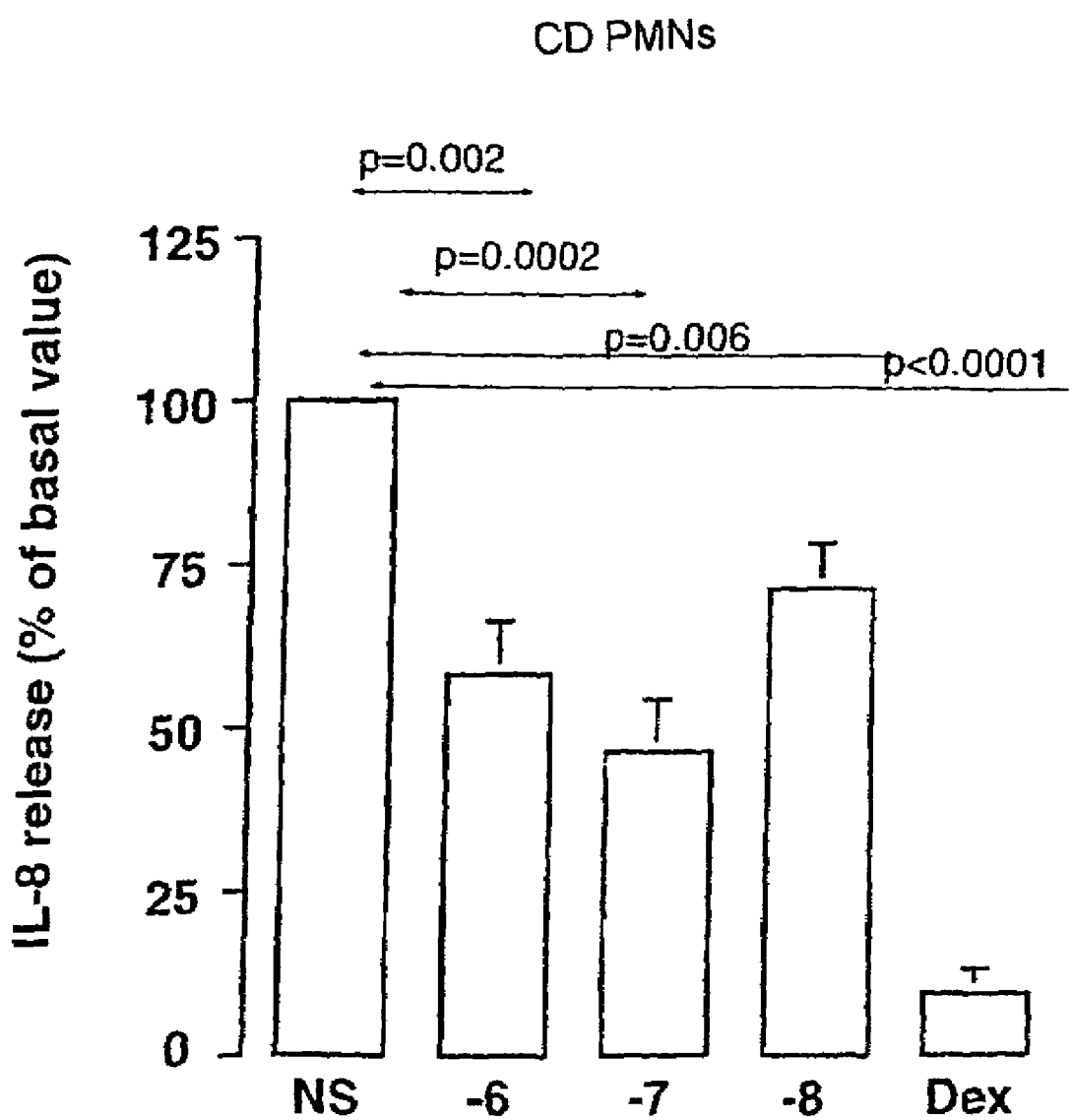
FIG. 4: The effect of the stimulation of cortico-dependant (CD) polynuclear neutrophils by peptide no. 1 is represented (NS=non-stimulated, DEX=dexamethasone).

The effect of the stimulation of cortico-dependant (CD) polynuclear neutrophils by peptide no. 1 is represented in FIG. 4 (NS=non-stimulated, DEX=dexamethasone).

These results show us that the activity of peptide no. 1 in the table is 10 times greater than that of dexamethasone.

---

The invention claimed is:

1. A cosmetic product comprising a compound of formula (I)

$$R\text{-}V^1\text{-}Ala^2\text{-}His^3\text{-}X^4\text{-}Y^5\text{-}Trp^6\text{-}NH_2 \quad \text{(I) (SEQ ID NO: 1)}$$

wherein

R represents a hydrogen atom or a protective group selected from the group consisting of an acetyl group, a benzoyl group, a tosyl group, a benzenesulfonyl group, a benzyloxycarbonyl group and a pyridinepropionyl group;

V represents an unnatural, L-configuration amino acid selected from the group consisting of norleucine, norvaline and 2-N-Me-norleucine;

X represents a natural or unnatural, L- or D-configuration amino acid which is aromatic in nature selected from the group consisting of phenylalanine, 1-naphthylalanine, 2-naphthylalanine, phenylglycine, benzothienylalanine, 4,4'-biphenylalanine, 3,3-diphenylalanine, indanylglycine, 4-methylphenylalanine, thienylalanine, and p-nitrophenylalanine; and Y represents a natural or unnatural, L-configuration amino acid which is basic in nature selected from the group consisting of arginine, lysine and ornithine; enantiomers or diastereoisomers and mixtures thereof, and wherein, the amino acids Ala, His and Trp at positions 2, 3 and 6, respectively, are in the L configuration wherein the product is effective in (1) protecting skin against sun exposure and for accelerating tanning of the skin, (2) recoloring white hair, and (3) soothing skin.

2. A dermocosmetic composition comprising a compound of formula (I)

$$R\text{-}V^1\text{-}Ala^2\text{-}His^3\text{-}X^4\text{-}Y^5\text{-}Trp^6\text{-}NH_2 \quad \text{(I) (SEQ ID NO: 1)}$$

wherein

R represents a hydrogen atom or a protective group selected from the group consisting of an acetyl group, a benzoyl group, a tosyl group, a benzenesulfonyl group, a benzyloxycarbonyl group and a pyridinepropionyl group;

V represents an unnatural, L-configuration amino acid selected from the group consisting of norleucine, norvaline and 2-N-Me-norleucine;

X represents an unnatural, L- or D-configuration amino acid which is aromatic in nature selected from the group consisting of phenylalanine, 1-naphthylalamine, 2-naphthylalanine, phenylglycine, benzothienylalanine, 4,4'-biphenylalanine, 3,3-diphenylalanine, indanylglycine, 4-methylphenylalanine, thienylalanine, and p-nitrophenylalanine; and Y represents a natural or unnatural, L-configuration amino acid which is basic in nature selected from the group consisting of arginine, lysine and ornithine; enantiomers or diastereoisomers and mixtures thereof, and wherein, the amino acids Ala, His and Trp at positions 2, 3 and 6, respectively, are in the L configuration wherein the composition is in the form of a solution, a lotion, an emulsion, a liquid aerosol or a sprayed aerosol a gel or a cream for topical application.

3. The cosmetic product of claim 1 wherein

R represents a protective group selected from the group consisting of an acetyl group, a benzenesulfonyl group and a pyridinepropionyl group;

V represents an unnatural amino acid selected from the group consisting of norleucine and 2-N-Me-norleucine, which is in the L configuration;

X represents an unnatural amino acid which is aromatic in nature selected from the group consisting of phenylanine, 2-naphthylalanine, thienylanine and p-nitrophenylalanine which is in the D or L configuration; and Y represents an, L-configuration amino acid which is basic in nature selected from the group consisting of arginine and lysine, enantiomers or diasteroisomers and mixtures thereof, and wherein the amino acids Ala, His and Trp at positions 2, 3 and 6, respectively, are in the L configuration.

4. The dermocosmetic preparation of claim 2 wherein
R represents a protective group selected from the group consisting of an acetyl group, a benzenesulfonyl group and a pyridinepropionyl group;
V represents an unnatural amino acid selected from the group consisting of norleucine and 2-N-Me-norleucine, which is in the L configuration;
X represents an unnatural amino acid which is aromatic in nature selected from the group consisting of phenylanine, 2-naphthylalanine, thienylalanine and p-nitrophenylalanine which is in the D or L configuration; and
Y represents an, L-configuration amino acid which is basic in nature selected from the group consisting of arginine and lysine, enantiomers or diasteroisomers and mixtures thereof, and
wherein the amino acids Ala, His and Trp at positions 2, 3 and 6, respectively, are in the L configuration.

5. The cosmetic product of claim 1 wherein the compound is selected from the group consisting of
Ac-Nle-Ala-His-DPhe-Arg-Trp-NH$_2$,
Ac-Nle-Ala-His-DPhe-Lys-Trp-NH$_2$,
Ac-Nle-Ala-His-DThi-Arg-Trp-NH$_2$,
BzlSO$_2$-Nle-Ala-His-DPhe-Arg-Trp-NH$_2$,
Tos-Nle-Ala-His-DPhe-Arg-Trp-NH$_2$,
BzlSO$_2$-Nle-Ala-His-DPhe-Lys-Trp-NH$_2$,
BzlSO$_2$-Nle-Ala-His-DpNO$_2$Phe-Lys-Trp-NH$_2$,
BzlSO$_2$-Nle-Ala-His-DThi-Lys-Trp-NH$_2$,
Ac-Nle-Ala-His-DThi-Lys-Trp-NH$_2$,
PyrProp-Nle-Ala-His-DpNO$_2$Phe-Lys-Trp-NH$_2$,
PyrProp-Nle-Ala-His-DpNO$_2$Phe-Arg-Trp-NH$_2$,
Ac-Nle-Ala-His-L$_2$,Nap-Lys-Trp-NH$_2$, enantiomers or diastereoisomers and mixtures thereof.

6. The dermocosmetic preparation of claim 2 wherein the compound is selected from the group consisting of
Ac-Nle-Ala-His-DPhe-Arg-Trp-NH$_2$,
Ac-Nle-Ala-His-DPhe-Lys-Trp-NH$_2$,
Ac-Nle-Ala-His-Dthi-Arg-Trp-NH$_2$,
BzlSO$_2$-Nle-Ala-His-DPhe-Arg-Trp-NH$_2$,
Tos-Nle-Ala-His-DPhe-Arg-Trp-NH$_2$,
BzlSO$_2$-Nle-Ala-His-DPhe-Lys-Trp-NH$_2$,
BzlSO$_2$-Nle-Ala-His-DpNO$_2$Phe-Lys-Trp-NH$_2$,
BzlSO$_2$-Nle-Ala-His-DThi-Lys-Trp-NH$_2$,
Ac-Nle-Ala-His-DThi-Lys-Trp-NH$_2$,
PyrProp-Nle-Ala-His-DpNO$_2$Phe-Lys-Trp-NH$_2$,
PyrProp-Nle-Ala-His-DpNO$_2$Phe-Arg-Trp-NH$_2$,
Ac-Nle-Ala-His-L2,Nap-Lys-Trp-NH$_2$, enantiomers or diastereoisomers and mixtures thereof.

* * * * *

UNITED STATES PATENT AND TRADEMARK OFFICE
CERTIFICATE OF CORRECTION

PATENT NO. : 7,268,108 B2
APPLICATION NO. : 10/503090
DATED : September 11, 2007
INVENTOR(S) : Anne-Marie Pinel It is certified that error appears in the above-identified patent and that said Letters Patent is hereby corrected as shown below:

Column 1, line 64, please correct the following:
"His=histidine, Phe=phenylalanifle, Arg=arginine" should read --His=histidine, Phe=phenylalanine, Arg=arginine--

Column 3, line 48, please correct the following:
"peptide no. 1 is respresented (NS=non-stimulated," should read --peptide no. 1 is represented (NS=non-stimulated,--

Claim 2, column 14, line 33, please correct the following:
"X represents an unnatural, L- or D-configuration amino" should read --X represents a natural or unnatural, L- or D-configuration amino--

Claim 3, column 14, line 58, please correct the following:
"X represents an unnatural amino acid which is aromatic in" should read --X represents a natural or unnatural amino acid which is aromatic in--

Claim 3, column 14, line 62, please correct the following:
"Y represents an, L-configuration amino acid which is" should read --Y represents a natural, L-configuration amino acid which is--

Claim 4, column 15, line 8, please correct the following:
"X represents an unnatural amino acid which is aromatic in" should read --X represents a natural or unnatural amino acid which is aromatic in--

Claim 4, column 15, line 12, please correct the following:
"Y represents an, L-configuration amino acid which is" should read --Y represents a natural, L-configuration amino acid which is--

Claim 5, column 16, line 6, please correct the following:
"Ac-Nle-Ala-His-$L_2$,Nap-Lys-Trp-$NH_2$ enantiomers or" should read --Ac-Nle-Ala-His-L2,Nap-Lys-Trp-$NH_2$ enantiomers or--

UNITED STATES PATENT AND TRADEMARK OFFICE
CERTIFICATE OF CORRECTION

PATENT NO. : 7,268,108 B2
APPLICATION NO. : 10/503090
DATED : September 11, 2007
INVENTOR(S) : Anne-Marie Pinel It is certified that error appears in the above-identified patent and that said Letters Patent is hereby corrected as shown below:

Claim 6, column 16, line 12, please correct the following:
"Ac-Nle-Ala-His-Dthi-Arg-Trp-$NH_2$," should read
--Ac-Nle-Ala-His-DThi-Arg-Trp-$NH_2$,--

Signed and Sealed this

First Day of April, 2008

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Norleucine, Norvaline or
      2-N-Me-Norleucine
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (4)..(4)
<223> OTHER INFORMATION: Xaa can be phenylalanine, 1-naphtylalanine,
      2-naphtylalanine, phenylglycine, benzothienylalanine,
      4,4'-biphenylalanine, 3,3-diphenylalanine, homophenylalanine,
      indanylglycine, 4-methylphenylalanine, thienylalanine,
      p-nitro-phenylalanine, or halogenophenylalanine
<220> FEATURE:
<221> NAME/KEY: misc_feature
<222> LOCATION: (5)..(5)
<223> OTHER INFORMATION: Xaa can be Arginine, Lysine, or Ornithine
<220> FEATURE:
<221> NAME/KEY: MOD_RES
<222> LOCATION: (6)..(6)
<223> OTHER INFORMATION: AMIDATION

<400> SEQUENCE: 1

Xaa Ala His Xaa Xaa Trp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Norleucine, Norvaline or
      2-N-Me-Norleucine
<220> FEATURE:
<221> NAME/KEY: MOD_RES
<222> LOCATION: (1)..(1)
<223> OTHER INFORMATION: ACETYLATION
```

-continued

```
<220> FEATURE:
<221> NAME/KEY: misc_feature
<222> LOCATION: (4)..(4)
<223> OTHER INFORMATION: Xaa = 2-naphtylalanine
<220> FEATURE:
<221> NAME/KEY: MOD_RES
<222> LOCATION: (6)..(6)
<223> OTHER INFORMATION: AMIDATION

<400> SEQUENCE: 2

Xaa Ala His Xaa Lys Trp
1               5

<210> SEQ ID NO 3
<211> LENGTH: 13
<212> TYPE: PRT
<213> ORGANISM: Artificial Sequence
<220> FEATURE:
<223> OTHER INFORMATION: Alpha-MSH tridecapeptide

<400> SEQUENCE: 3

Ser Tyr Ser Met Glu His Phe Arg Trp Gly Lys Pro Val
1               5                   10
```